United States Patent
Arizti et al.

(10) Patent No.: US 7,708,728 B2
(45) Date of Patent: *May 4, 2010

(54) ABSORBENT ARTICLES WITH COMFORTABLE ELASTICATED LAMINATES

(75) Inventors: Blanca Arizti, Frankfurt (DE); Ekaterina Anatolyevna Ponomarenko, Bad Soden (DE); Simone Seeboth, Schwalbach (DE); Gemma Baquer-Molas, Schwalbach (DE)

(73) Assignee: The Procter & Gamble Company, Cincinnati, OH (US)

( * ) Notice: Subject to any disclaimer, the term of this patent is extended or adjusted under 35 U.S.C. 154(b) by 134 days.

This patent is subject to a terminal disclaimer.

(21) Appl. No.: 11/582,188

(22) Filed: Oct. 17, 2006

(65) Prior Publication Data
US 2007/0088307 A1  Apr. 19, 2007

(30) Foreign Application Priority Data
Oct. 18, 2005  (EP) .................................. 05109670

(51) Int. Cl.
A61F 13/15 (2006.01)
A61F 13/20 (2006.01)

(52) U.S. Cl. .................... 604/385.27; 604/385.24; 604/385.01

(58) Field of Classification Search ............... 604/367, 604/381–382, 385.01, 385.24–385.28
See application file for complete search history.

(56) References Cited

U.S. PATENT DOCUMENTS

| | | | |
|---|---|---|---|
| 3,911,173 A | 10/1975 | Sprague, Jr. | |
| 3,929,135 A | 12/1975 | Thompson | |
| 4,324,246 A | 4/1982 | Mullane et al. | |
| 4,342,314 A | 8/1982 | Radel et al. | |
| 4,463,045 A | 7/1984 | Ahr et al. | |
| 4,573,986 A | 3/1986 | Minetola et al. | |
| 4,609,518 A | 9/1986 | Curro et al. | |
| 4,629,643 A | 12/1986 | Curro et al. | |
| 4,785,996 A | 11/1988 | Ziecker et al. | |
| 4,842,666 A | 6/1989 | Wierenicz | |
| 5,006,394 A | 4/1991 | Baird | |
| 5,322,729 A | 6/1994 | Heeter et al. | |
| 5,342,342 A * | 8/1994 | Kitaoka ................. | 604/385.19 |
| 5,571,096 A | 11/1996 | Dobrin et al. | |
| 5,607,760 A | 3/1997 | Roe | |
| H1732 H | 6/1998 | Johnson | |
| 5,865,823 A | 2/1999 | Curro | |
| 5,876,753 A | 3/1999 | Timmons et al. | |
| 5,888,591 A | 3/1999 | Gleason et al. | |

(Continued)

FOREIGN PATENT DOCUMENTS

EP  1 072 243 A2 *  1/2001

(Continued)

*Primary Examiner*—Michele Kidwell
(74) *Attorney, Agent, or Firm*—John G. Powell; William E. Gallagher

(57) ABSTRACT

An absorbent article comprising a topsheet with a large opening for receiving feces. The topsheet has an elastic laminate portion with y-direction elongation. The laminate portion has a first zone, a second zone and, optionally, a third zone. The zones have different degrees of maximum elongation and/or different wrinkle heights and/or densities. The zones are configured such that one or more zones are created that cause less or no pressure marks. Overall, the topsheet maintains an excellent force profile, resulting in well performing, comfortable to wear absorbent articles that provide isolation of feces away from the skin.

7 Claims, 9 Drawing Sheets

U.S. PATENT DOCUMENTS

| | | |
|---|---|---|
| 5,938,648 A | 8/1999 | LaVon et al. |
| 6,045,877 A | 4/2000 | Gleason et al. |
| 6,482,191 B1 | 11/2002 | Roe et al. |
| 2003/0004489 A1 * | 1/2003 | Ashton et al. .......... 604/385.25 |
| 2005/0095942 A1 | 5/2005 | Mueller et al. |

FOREIGN PATENT DOCUMENTS

| | | |
|---|---|---|
| WO | WO 95/16746 A1 | 6/1995 |
| WO | WO 96/03501 A1 | 2/1996 |

* cited by examiner

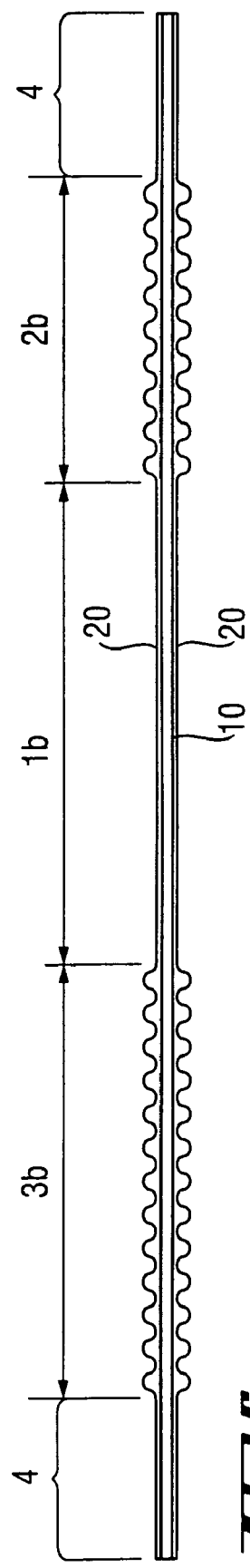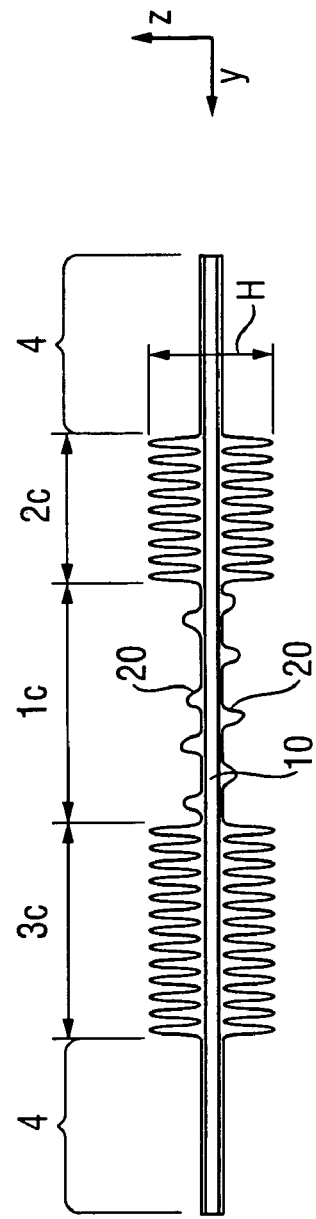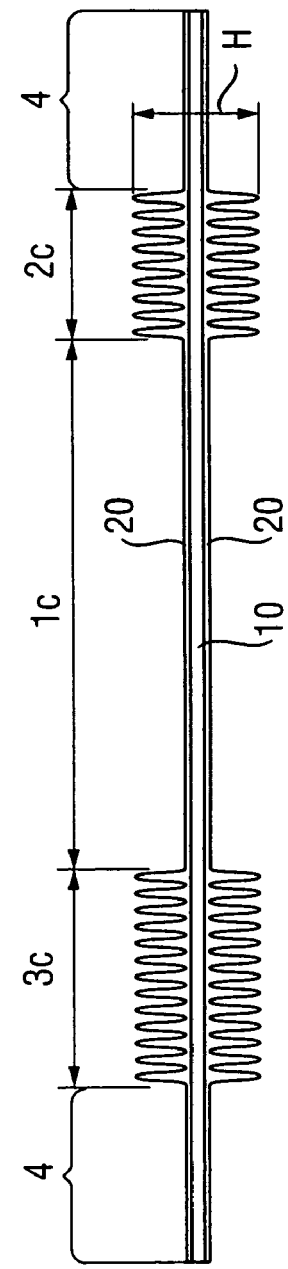
Fig. 6
Fig. 7
Fig. 8

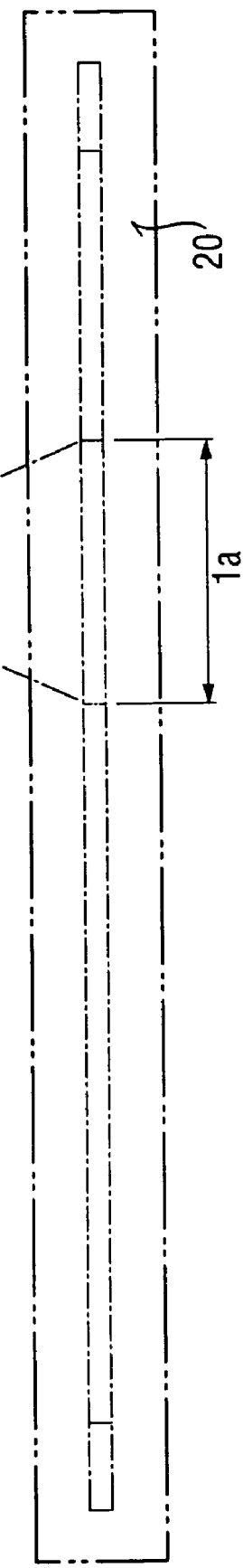
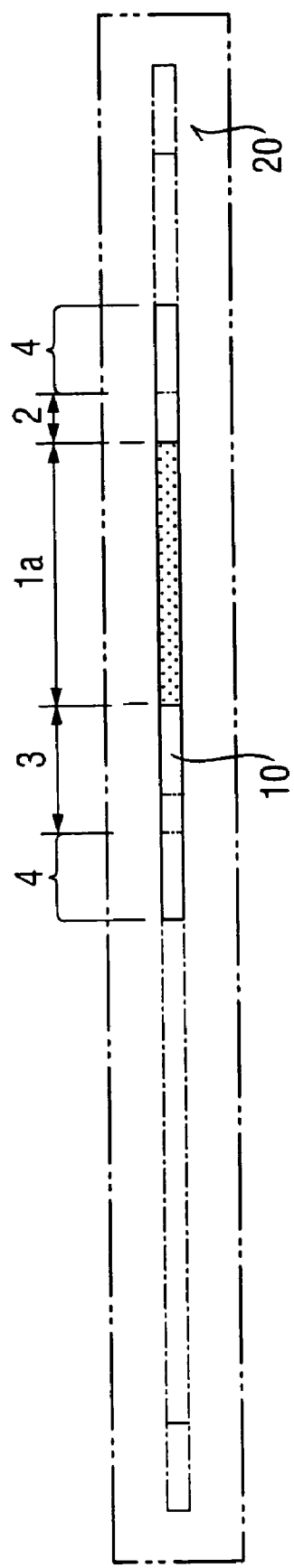
Fig. 9
Fig. 10

ABSORBENT ARTICLES WITH COMFORTABLE ELASTICATED LAMINATES

FIELD OF THE INVENTION

This invention relates to absorbent articles comprising a component that comprises an elastic laminate with elongation (stretch) along a first direction, comprising a support sheet and an elastic material and zones wherein each zone has a different degree of maximum elongation, different wrinkle heights and/or different wrinkle densities.

BACKGROUND OF THE INVENTION

Absorbent articles such as infant diapers, training pants and adult incontinence garments typically comprise elastic leg cuffs and or barrier cuffs to reduce leakage of exudates from the article. Often, they also comprise an elasticated waist band, to improve the fit and comfort when the wearer is moving. A certain type of diapers for feces isolation comprises (also) a topsheet with a large opening with there along elastic bands to ensure correct alignment of the topsheet and the opening with the anus of the user, and to thus ensure optimum reception and isolation of the feces under the topsheet.

These elasticated portions of such articles typically comprise an elastic material laminated to a non-elastic sheet, such as a plastic film, or nonwoven material, obtained by attaching the elastic material in stretched state to the sheet. The resulting laminate thus comprises in unstretched, contracted state and in partially stretched state a surplus of sheet material that forms wrinkles.

Such elasticated portions of the diaper can be uncomfortable in use, due to the pressure of the elastic portions on the skin and/or due to rubbing of the wrinkled elasticated portions over the skin.

The inventors have also found that even if the user does not experience the elasticated portions as uncomfortable, the red skin marks caused by the elasticated portions may still be perceived by the care taker as uncomfortable for the user.

The inventors have also found that in use the most stringent problem is the presence of pressure marks close to the sensitive areas of the users, e.g., the genitals. They found surprisingly that provided the pressure marks are reduced on the skin close to the genitals, the diaper will be (perceived to be) more comfortable.

The inventors have found that by providing elastic portions in the elasticated topsheet of the absorbent article (diaper), that have a (small) zone with only a minor degree of elastication, or no elastication at all, that correspond in use with these sensitive areas, and that have (larger) zones with higher degrees of elastication, an absorbent article (e.g., diaper) is obtained that still maintain an excellent elastic profile and performance and at the same type has a highly reduced, or no, pressure mark problem and that is more comfortable in use. At the same time, the excellent force profile still ensures that the topsheet remains in close proximity of the skin of the user and that the exudates (feces) are received through the opening and kept away from the skin (isolated).

SUMMARY OF THE INVENTION

The invention relates to a disposable absorbent article, comprising a topsheet having an opening (for receiving feces) with longitudinal (y-direction) edges, and having one or more elastic laminate portions, formed by elastic material attached to the topsheet, said elastic laminate portions being positioned along at least part of the longitudinal edges of said opening, said topsheet and elastic laminate portion(s) being elastically stretchable along a first direction (e.g., y-direction), whereby said elastic laminate portion has an absolute contracted length $L_c$ and a fully stretched absolute length $L_s$, and whereby said elastic laminate portion can be elongated with a maximum elongation $\epsilon$ of at least 0.6, or at least 0.8, and whereby:

said laminate portion has (in y-direction) zones with different maximum elongation, including a first zone with an absolute contracted length $L_{czone1}$ and an absolute stretched length $L_{szone1}$ and a maximum elongation $\epsilon_{zone1}$ of less than 50% of $\epsilon$, and a second zone with an absolute contracted length $L_{czone2}$ and an absolute stretched length $L_{szone2}$ and with a maximum y-direction elongation $\epsilon_{zone2}$ of more than $\epsilon$, said first zone and second zone having an absolute contracted length $L_{czone1}$ and $L_{czone2}$ of at least 2 cm.

The invention also related to a disposable absorbent article comprising a topsheet having an opening (for receiving feces) with longitudinal (y-direction) edges, and having one or more elastic laminate portions, formed by elastic material attached to the topsheet, said elastic laminate portions being positioned along at least part of the longitudinal edges of said opening, said topsheet and laminate portion being elastically stretchable along a first direction (e.g., y-direction), and said elastic laminate portion having a fully stretched absolute length $L_s$ and an absolute contracted length $L_c$, and whereby said elastic laminate portion can be elongated with an elongation $\epsilon$ of at least 0.6 or at least 0.8, whereby:

said elastic laminate portion has zones (in y-direction) of different maximum elongation, having at least a first zone with an absolute contracted length $L_{czone1}$ and an absolute stretched length $L_{szone1}$ and a maximum y-direction elongation $\epsilon_{zone1}$ and a second zone with an absolute contracted length $L_{czone2}$ and an absolute stretched length $L_{szone2}$ and with a maximum elongation $\epsilon_{zone2}$, and whereby said first zone and said second zone each have an absolute contracted length $L_{czone1}$ of at least 2 cm, and whereby at a partial elongation $\epsilon=0.5$, a) said elastic laminate portion has wrinkles with an average wrinkle height (in z-direction) $H_w$, and said first zone has no wrinkles or wrinkles with an average wrinkle height $H_{wzone1}$ of less than 50% of $H_w$, and/or b) said elastic laminate portion has a wrinkle density $D_w$ (wrinkles per cm) and said first zone has a wrinkle density $D_{wzone1}$ of 0 or of less than 50% of $D_w$.

The article may be a disposable absorbent article, such as, for example, a diaper, an adult incontinence garment, training pants or the like.

The opening may be an elongated slit opening.

The elastic laminate portion may comprise at least three zones wherein the first zone is positioned between the second and third zone (in the direction of stretch). The first zone may be positioned in the crotch region of the article, or in the front 50% of the article. The contracted length of the second zone may be more than the contracted length of the first zone. Optionally, the elastic laminate portion may comprise on either or both longitudinal end (an) attachment portion(s) of less than 1.5 cm long or less than 1 cm long, where the elastic laminate portion has a reduced elongation potential, e.g., like the first zone.

BRIEF DESCRIPTION OF THE DRAWINGS

FIG. 6 shows a cross-sectional side-view of a laminate portion (10) of FIGS. 2 and 3 in a partially stretched state.

FIG. 7 shows a cross-sectional side-view of the laminate portion (10) in a contracted state.

FIG. 8 shows a cross-sectional side-view of an alternative laminate portion in contracted state whereby the first zone (1c) does not comprise any wrinkles and has no elongation potential.

FIGS. 9 to 11 show a schematic top-view of how the elastic laminate portions (10) and the topsheet (20) herein may be obtained.

DETAILED DESCRIPTION

Figure 1:
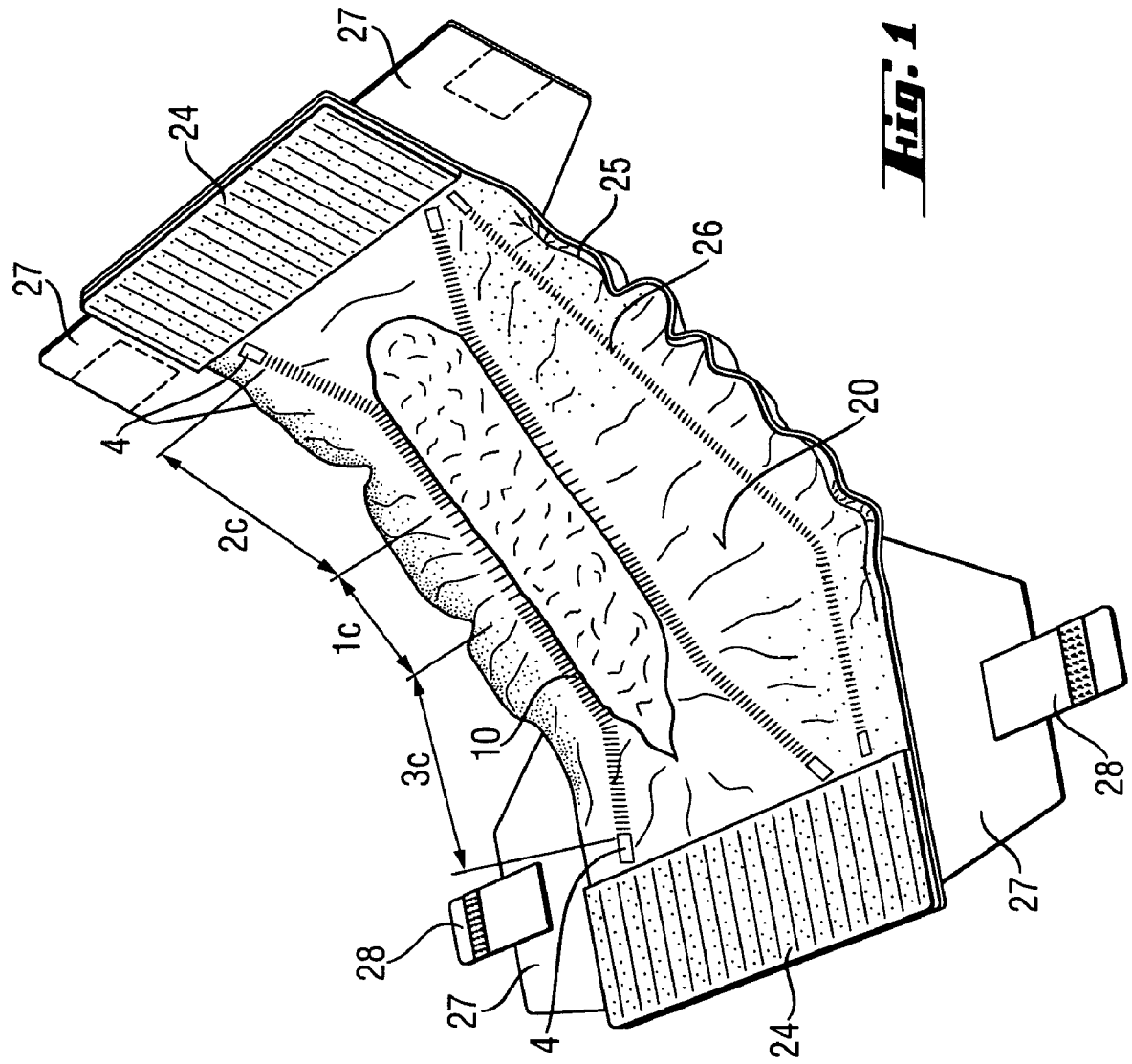
FIG. 1 shows a perspective view of an exemplary diaper of the present invention having a topsheet (20), i.e., a topsheet (20), with a two separate, distinct elastic laminate portions (10) that each have a first zone (1c) with only very limited elongation potential.

"Absorbent article" refers to wearable devices, which absorb and/or contain liquid, and more specifically, refers to devices, which are placed against or in proximity to the body of the wearer to absorb and contain the various exudates discharged from the body. As used herein, the term "diaper" refers to an absorbent article generally worn by infants and incontinent people about the lower torso.

"Y-direction" elongation or stretch as used herein means that the topsheet (20) or laminate portion (10) has as a whole an elongation or stretch in an average direction, that is herein referred to as "y-direction". This may be a direction within 45 degrees of the longitudinal axis or line parallel thereto of the topsheet (20) or elastic laminate portion (10).

"Absolute fully stretched length" is the length of the topsheet (20) or elastic laminate portion (10) when said topsheet (20) or portion (10) is stretched in y-direction as set out herein to its maximum length.

"Absolute contracted length" is the length of the topsheet (20) or elastic laminate portion (10), when no stretching force is applied to it, e.g., when it is in relaxed state, flat on a surface.

The "z-direction" is perpendicular to the y-direction and substantially in the direction of the wrinkle height in the laminate, and is herein also referred to as the height or thickness dimension.

The "x-direction" is perpendicular to both the x- and y-directions.

As used herein, "elastic" means, that the item is extendible or stretchable by application of a force in a certain direction and returns to at least 80% of its original length but to less than 150% of its original length in that direction, and typically to about its original size, after the stretching force is released.

As used herein, "along" means at least partially parallel and in close proximity or even in contact with.

As used herein, the opening in the topsheet is an area completely circumscribed by the topsheet, but where the topsheet material is not present, and which is large enough to receive fecal material, typically being at least 2 cm long or wide, or having a surface area of at least 2 cm$^2$.

As used herein, the term "void space" is a cavity in the article present in at least the relaxed state, which serves to accept and contain bodily exudates such as fecal material, typically being at least 5 cm$^3$ in relaxed state.

As used herein "attached" includes "directly attached" and "indirectly attached".

Each embodiment defined by certain properties or dimension for which a value is defined herein is to be understood to include embodiments with functional equivalent properties or dimensions, e.g., a dimension of 0.5 cm has to be understood as meaning "about 0.5 cm." The disposable absorbent article of the invention may be a sanitary napkin, panty-liner, or a diaper, i.e., an adult incontinence garment or infant diaper (as shown in the FIGS. 1 to 5) or training or pull-up pants. The article comprises the topsheet (20) with an elastic laminate portion (10), described herein, and additional components, to have typically at least a backsheet (21), absorbent core and a core cover sheet or topsheet (20).

The absorbent article of the invention comprises at least a topsheet (20) comprising at least one elastic laminate portion (10), formed from an elastic material (12) and a part of said topsheet, e.g., the supporting topsheet material, that itself is typically not elastically stretchable, said elastic laminate portion (10) having at least y-directional stretch (elongation), or only y-directional stretch, as shown in the Figures. The article may also comprise other components that comprise such an elastic laminate portion (10), such as leg cuffs (25) or barrier cuffs (26) or a waist band (24).

The longest dimension or length of the topsheet (20) and of the elastic laminate portion(s) (10) are typically parallel to the y-axis of the topsheet (20) and article and is typically substantially parallel to the average direction of stretch of the elastic laminate portion (10) and topsheet (20).

If, for example, the leg cuffs (25) or barrier cuffs (26) comprise or consist of said elastic laminate portion (10) as well, then the y-direction of the leg cuffs (25) or barrier cuffs (26) and said laminate portion(s) (10) are typically substantially parallel or on average parallel to the y-direction and y-axis of the article.

Said topsheet (20) may comprise more than one of such laminate portions (10), which each may be identical in the first and second zones (1b, 2b) with regard to length and elongations thereof as referred to herein, or that may be different in the first and second zones (1b, 2b), with regard to lengths and elongations thereof. For example, the topsheet comprises at least two separate, distinct elastic laminate portions (10), each of which is positioned along at least a part of the opening, as described herein after.

The topsheet (20) may consist of a (supporting) topsheet material and the elastic material(s) (12) and optionally attachment means, like adhesive, and it may comprise additional elements as well. The topsheet material (20) may be a single sheet or it may comprise more than one sheet or layer, e.g., it may be a laminate of layers. It may be preferred that the topsheet (20) itself is not elastically stretchable in y-direction.

One example of an absorbent article according to the present invention is a diaper, as shown in FIGS. 1 to 5. The diaper may comprise an absorbent core, a liquid pervious core coversheet, positioned under the topsheet (20) and on the absorbent core, a liquid impervious backsheet (21), optionally (elastic) side panels (27), (elastic) leg cuffs (25), (elastic) barrier cuffs (26), (elastic) waist feature (24), and a fastening system (28). The article shown in FIGS. 1 and 3 has a first waist region, a second waist region opposed to the first waist region and a crotch region located between the first waist region and the second waist region, each region being about ⅓ of the length of the article.

In some embodiments, the backsheet (21) mat be impervious to liquids (e.g., urine) and may comprise a thin plastic film, such as a thermoplastic film, having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962 and X10964. Other suitable backsheet materials may include breathable materials which permit vapors to escape from the article while still preventing exudates from passing through the backsheet. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Exxon Chemical Co., of Bay City, Tex., under the designation EXXAIRE, and monolithic films such as manufactured by Clopay Corporation, Cincinnati, Ohio under the name HYTREL blend P18-3097. Some breathable composite materials are described in greater detail in PCT Application No. WO 95/16746 published on Jun. 22, 1995 in the name of E. I. DuPont; U.S. Pat. No. 5,938,648 issued on Aug. 17, 1999 to LaVon et al.; U.S. Pat. No. 5,865,823 issued on Feb. 2, 1999 in the name of Curro; and U.S. Pat. No. 5,571,096 issued to Dobrin et al. on Nov. 5, 1996.

The different parts or components of the article may be attached to one another by any means known in the art. For example, the attachment means may include a uniform continuous layer of adhesive, a patterned layer of adhesive, or an array of separate lines, spirals or spots of adhesive. One suitable attachment means comprises an open pattern network of filaments of adhesive as disclosed in U.S. Pat. No. 4,573,986 entitled "Disposable Waste-Containment Garment," which issued to Minetola et al. on Mar. 4, 1986. Other suitable attachment means include several lines of adhesive filaments swirled into a spiral pattern, as illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Adhesives found to be satisfactory are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, any other suitable attachment means or combinations of these attachment means as are known in the art.

The core coversheet may be compliant, soft-feeling and/or non-irritating to the wearer's skin. Further, at least a portion of the core cover sheet may be liquid pervious, permitting liquids to be absorbed by the absorbent core underneath. A suitable core cover sheet may be manufactured from a wide range of materials, such as porous foams, reticulated foams, apertured plastic films, or woven or nonwoven materials of natural fibers (e.g., wood or cotton fibers), synthetic fibers (e.g., polyester or polypropylene fibers), or a combination of natural and synthetic fibers. If the core cover sheet includes fibers, the fibers may be spunbond, carded, wet-laid, melt-blown, hydroentangled, or otherwise processed as is known in the art. One suitable core coversheet comprising a web of staple-length polypropylene fibers is manufactured by Veratec, Inc., a Division of International Paper Company, of Walpole, Mass. under the designation P-8. Suitable formed film core coversheets are described in U.S. Pat. No. 3,929,135, entitled "Absorptive Structures Having Tapered Capillaries" issued to Thompson on Dec. 30, 1975; U.S. Pat. No. 4,324,246 entitled "Disposable Absorbent Article Having A Stain Resistant Topsheet" issued to Mullane, et al. on Apr. 13, 1982; U.S. Pat. No. 4,342,314 entitled "Resilient Plastic Web Exhibiting Fiber-Like Properties" issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression" issued to Ahr, et al. on Jul. 31, 1984; and U.S. Pat. No. 5,006,394 "Multilayer Polymeric Film" issued to Baird on Apr. 9, 1991. Other suitable core coversheets may be made in accordance with U.S. Pat. Nos. 4,609,518 and 4,629,643 issued to Curro et al. on Sep. 2, 1986 and Dec. 16, 1986. Such formed films are available from The Procter & Gamble Company of Cincinnati, Ohio as "DRI-WEAVE" and from Tredegar Corporation of Terre Haute, Ind. as "CLIFF-T."

Any portion of the core coversheet or the topsheet (20) described herein may be coated with a lotion as is known in the art. Examples of suitable lotions include those described in U.S. Pat. No. 5,607,760 entitled "Disposable Absorbent Article Having A Lotioned Topsheet Containing an Emollient and a Polyol Polyester Immobilizing Agent" issued to Roe on Mar. 4, 1997. The lotion may function alone or in combination with another agent as the hydrophobizing treatment described above. The core coversheet and/or topsheet (20) may also include or be treated with antibacterial agents, some examples of which are disclosed in PCT Publication No. WO 95/24173 entitled "Absorbent Articles Containing Antibacterial Agents in the Topsheet For Odor Control" which was published on Sep. 14, 1995 in the name of Theresa Johnson.

The absorbent core may comprise any absorbent material which is generally compressible, conformable, non-irritating to the wearer's skin and capable of absorbing and retaining liquids such as urine and other certain body exudates. The absorbent core may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles, such as comminuted wood pulp, which is generally referred to as airfelt, and superabsorbent polymers or absorbent gelling materials; or any other known absorbent material or combinations of materials.

The article may also include a fastening system (28) that maintains the first waist region and the second waist region in a configuration so as to provide lateral tensions about the circumference of the article to hold it on the wearer. The fastening system (28) may comprise a surface fastener such as tape tabs, hook and loop fastening components and/or hermaphroditic fastening components; although any other known fastening means are generally acceptable. In alternative embodiments, opposing sides of the article may be seamed or welded to form a pant. This allows the article to be used as a pull-on type diaper or training pant. The term "training pants", as used herein, refers to disposable garments having fixed sides and leg openings designed for infant or adults wearers. Training pants (also referred in the art as "pull-on" products) are placed in position on the wearer by inserting the wearer's legs into the leg openings and sliding the training pant into position about the wearer's lower torso.

The article may also comprise side panels (27) that are elastic or non-elastically extensible to provide a more comfortable and contouring fit by initially conformably fitting the article to the wearer and sustaining this fit throughout the time of wear well past when it has been loaded with exudates since the elasticized or extensible side panels allow the sides of the article to expand and contract.

The article may include barrier cuffs (26) and/or leg cuffs (25) which provide improved containment of liquids and other body exudates. Said leg cuffs and/or barrier cuffs may also comprise the elastic laminate portion (10) as described herein below Topsheet (20) with the Elastic Laminate Portion(s) (10)

The topsheet (20) herein has at least one opening, or only one such opening, and said opening(s) may be in the form of a (single) slit opening. The opening may be present in (part of) the front region of the topsheet (20) (in use towards the front of the user) and in (part of) the back region of the topsheet (20). The topsheet (20) may also have a slit opening, which has a longitudinal dimension (length) substantially parallel to the longitudinal axis of the topsheet (20) and of the diaper.

In stretched state, the opening (or openings) of the topsheet (20) may be configured such that from 20% to 40% or from 20% to 30% of the length of the opening (or total length of the openings) extends from the transverse axis of the topsheet (20) towards the front edge of the topsheet (20), and the remaining percentage extends towards the back edge of the topsheet (20).

The dimensions and exact shape of the opening(s) may vary, depending on the size of the topsheet (20) and/or the absorbent article. For example, in one embodiment the opening may be in the form of a slit opening with substantially parallel longitudinal side edges, which are connected in the front and/or back by V-shaped or U-shaped edges, whereby both the front and back V-shaped edges comprise two angled edges. In another embodiment, the front V-shaped edges may have a larger angle than the back V-shaped edges. The front V-shaped edges may have an angle of from about 20° to 140°, from 45° to 65°, or from 55° to 60°, as described herein after and can be seen from FIGS. 1 and 2.

The maximum length of the slit opening may be, for example, from 40% to 90% or more, from 50% to 80% or from 60% to 70% of the total length, L, of the absorbent article.

In particular for size 4 diapers, it may be desirable to provide a maximum topsheet (20) length of between 45 cm and 55 cm, typically between 48 cm and 52 cm, such that the length of the single slit opening, when the diaper is in stretched state, is from 20 cm to 40 cm, or even from 25 cm to 35 cm, or even from 28 cm to 32 cm.

The average width of the opening herein, in stretched state, may be from 5% to 30% or from 10% to 25%, of the average width of the topsheet (20) (including opening width), or, for example, for a size 4 diaper, 15 mm to 60 mm or from 20 mm to 40 mm.

The topsheet (20) comprises at least one elastic laminate portion (10). For example, it may comprise at least two separate elastic laminate portions (10), as also shown in the Figures.

The elastic laminate portion (10) has at least two zones, a first zone (1) and a second zone (2) that have a different maximum elongation, as defined herein below, and/or that have a different wrinkle density and/or different wrinkle height, as defined herein. Each such zone is at least 2 cm, as can be understood from the test method below, for obtaining the stretched lengths and elongations of said zones.

Such zones may be obtainable by attaching to a topsheet (20) material one or more zones of an elastic material with a larger degree elongation than one or more other zone(s) of said elastic material.

Figure 15:
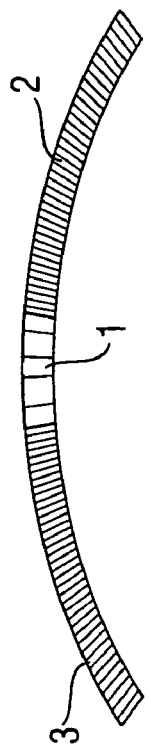
FIG. 15 shows a top-view of a curved laminate portion (10) in contracted state.

The elastic laminate portion (10) may be straight, curved, as shown in FIG. 15, or it may comprise several straight parts that are joined under an angle with one another, as can been seen in FIGS. 1 to 5 and 13, or a combination of such configurations. This is herein referred to, respectively, as "straight", "curved" or "angled" elastic laminate portion (10) s, respectively, or, for example, "curved and angled" elastic laminate portion (10), etc.

The elastic laminate portion (10) has an absolute contracted length $L_c$, which is determined as follows.

The topsheet (20) with the elastic laminate portion (10) is removed from the absorbent article, such that the elastic profile is not changed.

The topsheet (20) is placed as flat as possible on a surface, without applying any elongating force to it. Then the absolute contracted length of the elastic laminate portion (10) of the topsheet (20) is measured. This is herein referred to as the absolute contracted length of the laminate $L_c$.

The laminate portion (10) has a fully stretched absolute length $L_s$, and the laminate portion (10) has zones (1, 2) of different elongation, as defined herein, which can be detected by the method below and furthermore, each zone (1, 2) thereof has a contracted absolute length $L_{czone1,...x}$, and also a fully stretched absolute length $L_s$., $L_{szone1...x}$, which can be determined by the method described below and in the "Method" section, namely as follows:

1) When the Elastic Laminate Portion (10) is Straight:

2 cm long sections are marked on the laminate portion (10) (in contracted, e.g., relaxed state, as set out above), with a very fine marker pen, resulting in a multitude of 2 cm long sections along the y-axis and possibly one section of less than 2 cm.

Then, the whole laminate portion (10) is elongated as set out in the method below, so that the maximum or fully stretched length is obtained and then, this absolute fully stretched length can then be measured, which is herein referred to as $L_s$. The maximum elongation can then also be determined by: $\epsilon = (L_s - L_c)/L_c$.

Equally, the length of each section above that has been submitted to the method above and that may be elongated is measured.

The elongation of each section can be determined, as above, e.g.: $\epsilon_{section1} = (Ls_{section1} - 2 \text{ cm})/2 \text{ cm}$.

As defined herein, the laminate portion (10) has at least one section, herein referred to as first zone (1) that has an elongation of less than 50% of $\epsilon$. Typically, it has at least 2 consecutive sections that have an elongation of less than 50% of $\epsilon$, which together form the first zone (1).

Subsequently, the zones can be located and the contracted length $L_{czone1}$ can be determined (for example: 2 cm or 2×2 cm) and the fully stretched absolute length of such first zone $L_{szone1}$ can be determined (for example: 2.5 cm, or 2×2.2 . cm=4.4 cm), and the elongation of the first zone $\epsilon_{zone1}$ can be calculated as above.

A section that has an elongation of more than $\epsilon$ is herein referred to as a second zone (2), and if there are consecutive sections with an elongation of more than $\epsilon$, then they form together a second zone (2). For such a second zone (2), the $L_{czone2}$ can be determined (e.g., 2 cm or 2×2 cm, or 2×2 cm), and as above, the fully stretched absolute length of such second zone $L_{szone1}$ can be determined (for example: 4 cm, or 2×3.6 .cm=7.2 cm), and the elongation of the first zone $\epsilon_{zone1}$, as above.

Sections with an elongation of more than $\epsilon$ that are positioned on different sides (in y-direction) of the first zone (10) are herein referred to as different zones, e.g., second and third zone (2, 3).

Figure 3:
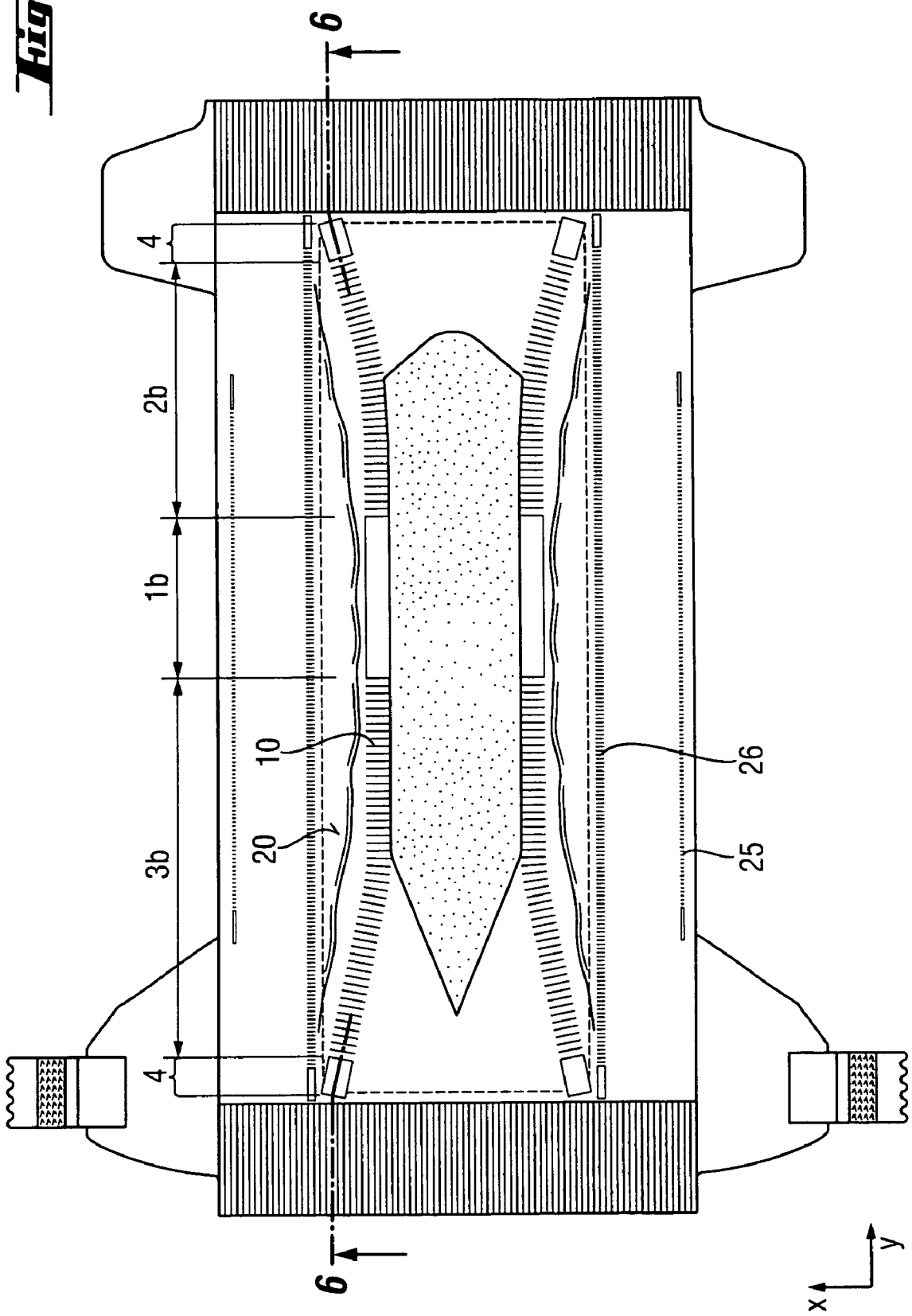
FIG. 3 shows a top view of a diaper in a partially stretched state, whereby the first zone (1b) is only very slightly elongated in comparison to FIG. 1 and it has no wrinkles.
Figure 13:
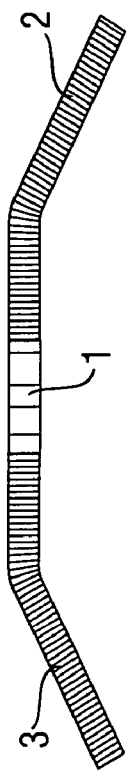
FIG. 13 shows a top-view of an angled laminate portion (10) in a contracted state.

2) When the Elastic Laminate Portion (10) is "Angled":

The laminate portion is divided by marking with a fine marker pen into straight parts (i.e., between the angles), for example, in 3 straight parts, as can be seen in FIGS. 3 and 13.

The contracted absolute length $L_c$ is obtained by adding up the contracted lengths of the straight parts of the laminate portion (10) (e.g., if it comprises 3 straight parts that are connected to one another with two angles, then the contracted absolute length of the 3 portions (10) are measured and added up.)

Then, each straight part is divided by a fine marker pen into sections of 2 cm length, and possibly a section of less than 2 cm. Subsequently, each straight part is elongated. The fully stretched absolute length of the laminate portion $L_s$ is obtained by adding up the fully stretched lengths of the straight parts of laminate portion (10). The elongation and stretched length of each section (e.g., of original contracted length of 2 cm) in each straight part are determined, and subsequently the first zone (1) and second zone (2) and optionally further zones (3, ...) are located and the lengths and elongations thereof can be determined, following the method as set out above with respect to a straight laminate portion (10).

3) When the Elastic Laminate Portion (10) is Curved:

The curved elastic laminate portion (10) is divided with a fine marker pen into sections of 2 cm absolute length and possibly one remaining section of a smaller length.

Each section has two transverse edge lines that are 2 cm apart, and each transverse edge line has a centre point. A line can be drawn through said two points of said two transverse edge lines. This will be the "y-direction line" along which the force will be applied in the method below, to elongate said section. This will be done for each section. Thus, the fully stretched length of each section and the elongation thereof can be determined.

After stretching all sections, a fully stretched absolute length of each section is measured. Then, the absolute stretched length of the laminate portion can be calculated by adding up these values for the different sections.

The first and second zone (1, 2) can then be located as set out above, and their fully stretched lengths and elongation can be determined as set out above.

4) Mixed Elastic Laminate Portions

If the elastic laminate portion (10) comprises a combination of curved, angled and/or straight parts, then a combination of the above methods is applied accordingly.

The elastic laminate portion (10) has an (e.g., substantially y-direction) elongation $\epsilon$ (maximum) of at least 0.6, at least 0.8, at least 1.0, at least 1.2 or at least 1.4.

The elastic laminate portion (10) has as least a first zone (1c) and a second zone (2c), and may include further zones (third zone (3c), fourth zone etc.) in the y-direction, with a different degree of maximum elongation potential in this y-direction, and/or a different wrinkle height and/or a different wrinkle density, each being at least 2 cm in contracted (relaxed) state, as can be seen from FIGS. 7 and 8.

The elastic laminate portion (10) may comprise at one or both longitudinal ends an attachment portion (4) where the elastic is attached to the supporting topsheet material and where there may not be any wrinkles, and that has an elongation of less than 0.2, or even 0. These attachment areas are typically very small, having a length of less than 2 cm, or typically less than 1.5 cm or even less than 1 cm, or even less than 0.5 cm. However, in another embodiment herein, the elastic laminate portion is attached to the topsheet material such that no such attachment portions (4) are formed on either longitudinal end thereof.

In another embodiment shown in FIG. 6, each zone ($1b$, $2b$, $3b$) has fully stretched absolute length ($L_{szone1}$, $L_{szone2}$, $L_{szone3}$ etc.) and a contracted absolute length ($L_{czone1}$, $L_{czone2}$, $L_{czone3}$ etc.) and a maximum elongation ($\epsilon_{zone1}$, $\epsilon_{zone2}$, $\epsilon_{zone3}$, etc.), determined as follows: $\epsilon_{zone1}=(L_{szone1}-L_{czone1})/L_{czone1}$, and so forth, whereby said values are obtained as set out above.

In another embodiment, the first zone ($1b$) has a maximum elongation $\epsilon_{zone1}$ which is much less than the average elongation $\epsilon$ of the whole elastic laminate portion (10) and consequently, the second zone ($2b$) at least has a maximum elongation $\epsilon_{zone2}$, which is more than the average elongation $\epsilon$ of the elastic laminate portion (10) as a whole.

Herein, the first zones $1a$, $1b$ and $1c$ are as follows: first zone ($1c$) in the elastic laminate portion (10) shows the contracted state; first zone ($1b$) in the elastic laminate portion (10) shows the partially stretched state; the elastic material is shown as first zone ($1a$). The same applies to the second and third zones ($2a$, $2b$, $2c$) and ($3a$, $3b$, $3c$).

Typically, $\epsilon_{zone1}$ is less than 50% of $\epsilon$, less than 40% of $\epsilon$, less than 30% of $\epsilon$ or less than 20% of $\epsilon$, or in one embodiment the first zone ($1c$) has no elongation potential and $\epsilon_{zone1}$ is 0. The latter can be seen in FIGS. 5 and 8, where the first zone ($1c$) has no wrinkles in contracted state ($1c$), and has no elongation potential.

The elastic laminate portion (10) herein has at least in contracted state and in partially stretched state (elongation=0.5) wrinkles formed from the topsheet material(s) (20).

In the first zone ($1c$), the average wrinkle height of the wrinkles may be less than the average wrinkle height of the wrinkles in the second (and optionally or preferably third) zone ($2c$, $3c$), and less than the average wrinkle height of the elastic laminate portion (10) as a whole (on average).

In one embodiment of the invention the absorbent article comprises a topsheet (20) with an elastic laminate portion (10) that has, at an elongation $\epsilon=0.5$ (as determined by the method described herein), an average wrinkle height ($H_w$) and the first zone ($1c$) has in this embodiment an average wrinkle height $H_{wzone1}$ of less than 50% of $H_w$, less than 30%, less than 20% of $H_w$ or even less than 10% $H_w$, or the first zone ($1c$) has even no wrinkles at all ($H_{wzone1}$ is about 0).

The second zone ($2c$) has typically an average wrinkle height $H_{wzone2}$ of at least 1.1 $H_w$, at least 1.2 $H_w$, at least 1.3 $H_w$, or at least 1.35 $H_w$.

$H_w$ may, for example, be between 600 microns and 1000 microns, or, for example, to 850 micron and $H_{wzone1}$ may be 300 microns or less or 200 microns or less, or even about 0. $H_{wzone2}$ may be from 700 to 1200 microns, or from 750 to 1000 microns.

In another embodiment, or in addition, the average wrinkles density (amount of wrinkles per cm lengthwise) is less in the first zone (1c) than in the second zone (2c) (and than in, for example, the third (3c)) zone) and less than the average wrinkle density of the elastic laminate portion (10) as a whole.

At an elongation $\epsilon$ of 0.5, the laminate portion (10) may have a wrinkle density $D_w$ (wrinkles per cm) and said first zone (1c) has, at an elongation $\epsilon$ of 0.5, a wrinkle density $D_{wzone1}$ of less than 50% of $D_w$, even less than 30% of $D_w$, or even less than 20% or even less than 10% of $D_w$, or even no wrinkles at all, i.e., a wrinkle density of about 0.

Typically, $D_w$ at this elongation of 0.5, is at least 7.5 wrinkles per cm. $D_{w1}$ may be 5 wrinkles per cm or less, or even 3 wrinkles per cm or less or even 0 wrinkles.

The second zone (2c) has an average wrinkle density of more than the average wrinkle density of the first zone (1c) and more than the average wrinkle density of the elastic laminate portion (10), being at least 1.1. $D_w$, or at least 1.2 $D_w$, or at least 1.25 $D_w$.

Figure 2:
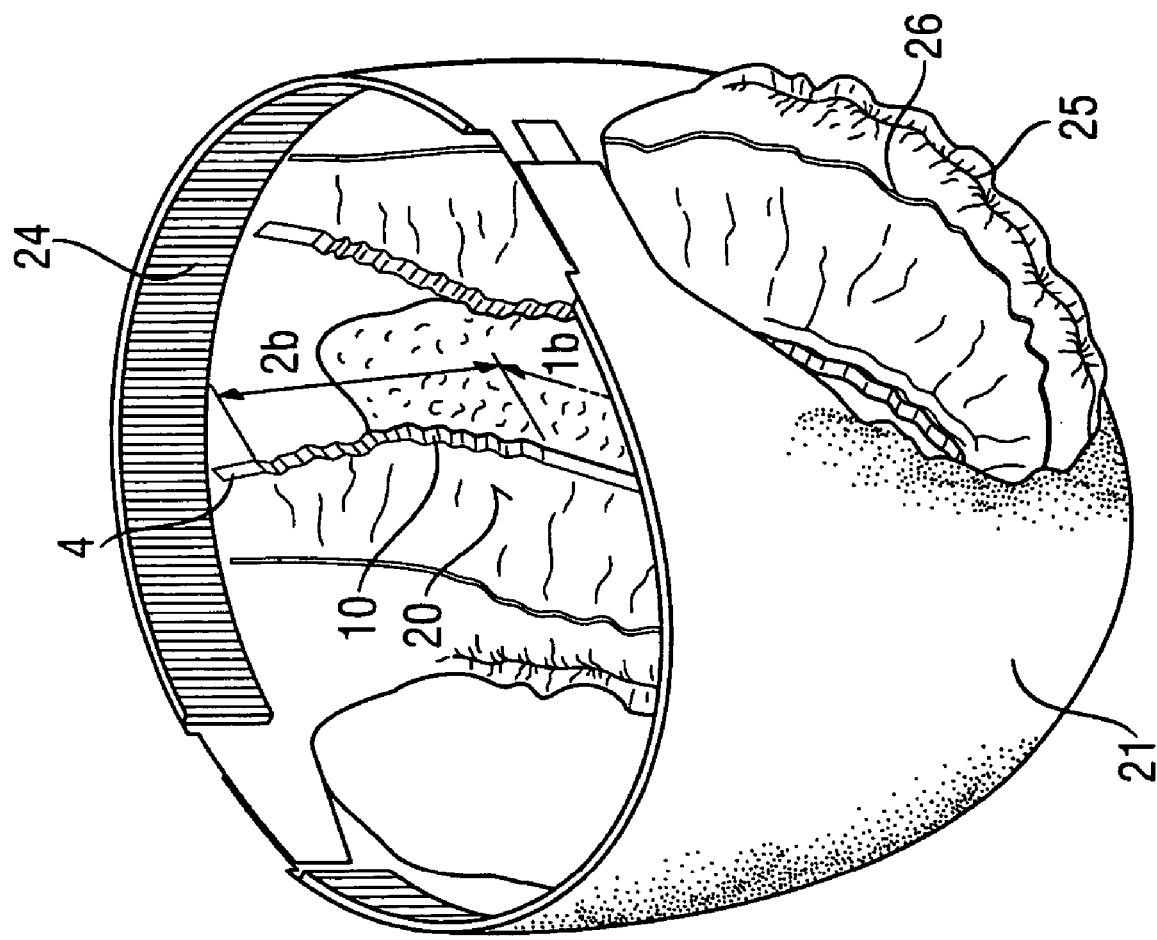
FIG. 2 shows a diaper in use, whereby the second zone (2b) is in a partially stretched state.
Figure 5:
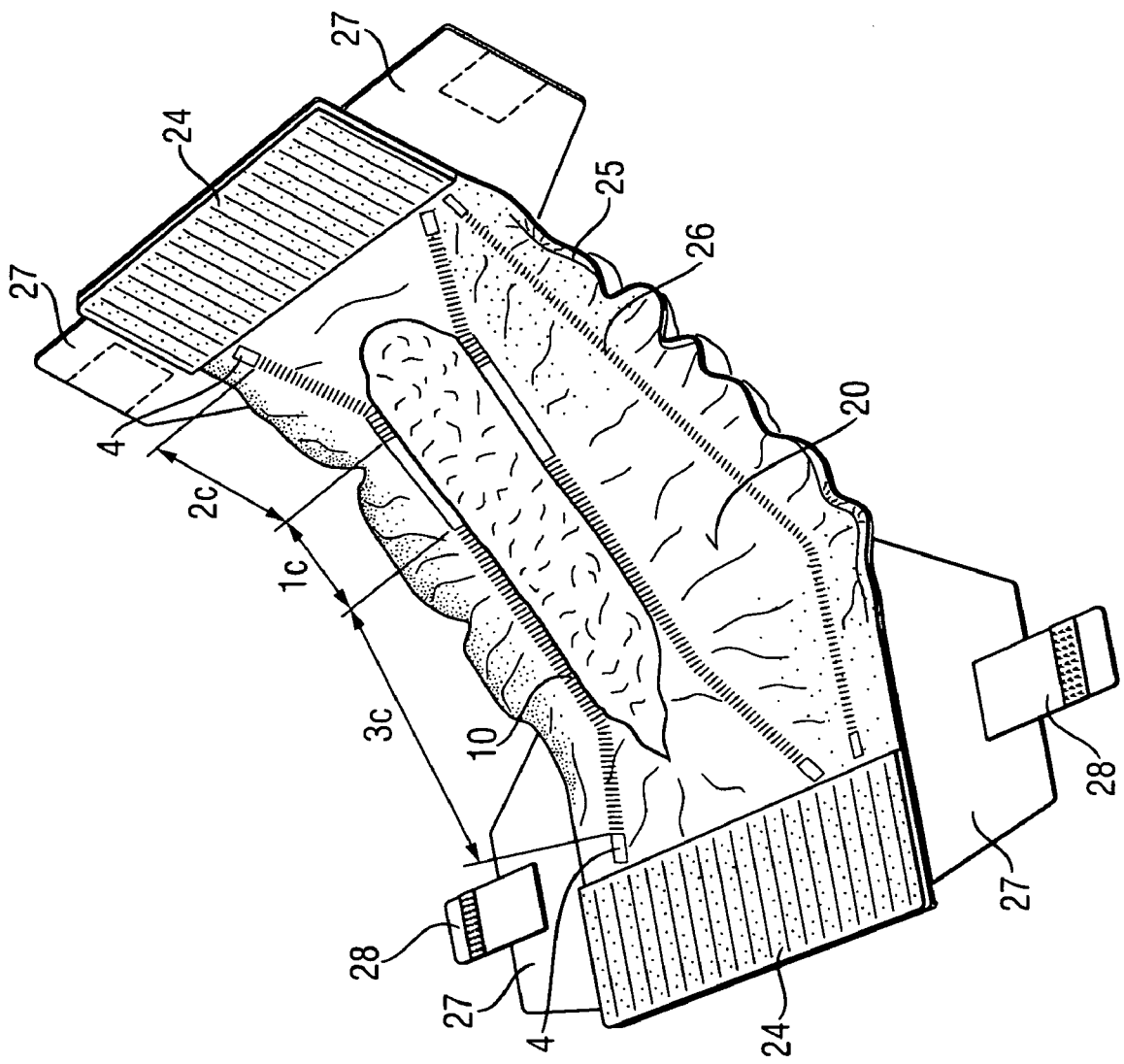
FIG. 5 shows a perspective view of an alternative diaper whereby the first zone (1c) does comprise elastic material but does not comprise any wrinkles even in contracted state.
Figure 11:
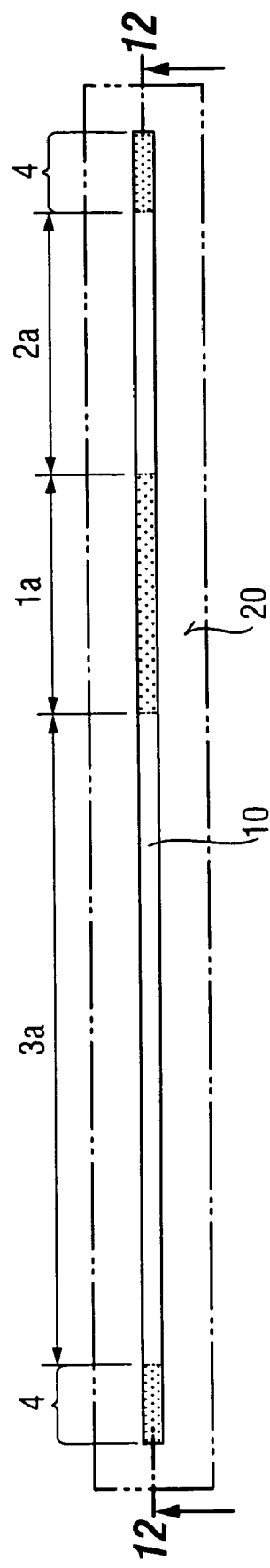
Figure 12:
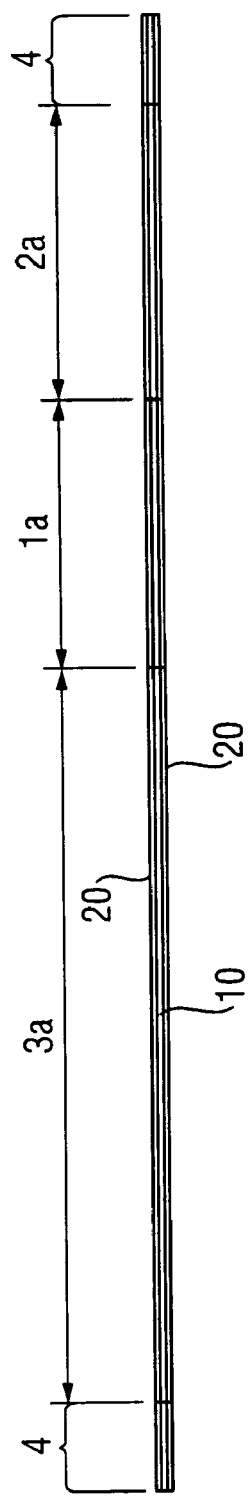
FIG. 12 shows a cross sectional side view of the resulting laminate (10) and topsheet (20).

In another embodiment, the first zone (1b, 1c) is in use positioned in contact with the skin area that is closest to the genitals, typically it may be positioned in the front 50% or even in the front 40% (length wise) of the article, as shown in FIG. 5 and possibly not in the front 10% or even not in the front 20% of the length of the article, or, for example, in the crotch region of the article, as shown in FIGS. 1 and 2. In another embodiment said first zone (1c) may, for example, be in closest proximity to the belly button.

The maximum elongation potential of the second zone (2), $\epsilon_{zone2}$ is more than $\epsilon$, 110% of $\epsilon$, or 120% of or even 130% of $\epsilon$.

The absolute contracted length of the first zone ($L_{czone1}$) is at least 2 cm, or it may be more, e.g., 2×2 cm, or 3×2 cm.

$L_{czone1}$ may be at least 20% or at least 30% of $L_c$, but typically at the most 60% $L_c$ or at the most 50%.

The second zone (2) may have the same length in contracted state $L_{czone2}$ as the first zone (1) above, or it may have a larger length than the first zone. It may be positioned in the back (length wise) 50% of the article, or, for example, in the back waist region.

The elastic laminate portion (10) may also comprise further zones, e.g., a third zone (3) with a maximum elongation $\epsilon_{zone3}$ of more than the maximum elongation of the first zone $\epsilon_{zone1}$, and typically more than the average maximum elongation $\epsilon$ of the whole elastic laminate portion (10), and this may be equal to the maximum elongation of the second zone $\epsilon_{zone2}$. It has an $L_{czone3}$ of at least 2 cm.

The first zone (1c) is typically positioned between the second (2c) and third zone (3c) (in the y-direction orientation). For example, if the second zone (2c) is located in the back 40% or 50% or 60% (lengthwise) of the article or component, then the third zone (3c) may be positioned in the front 30% or 20% or 10% (lengthwise) of the article or topsheet (20), e.g., in part of the front waist region, with the first zone (1c) therein between. Attachment portions (4) may or may not be present on both longitudinal ends of the elastic laminate portion (10).

Typically the third zone (3c) has an average wrinkle height $H_{wzone3}$ that is more than the average wrinkle height of the first zone $H_{wzone1}$, and typically that is more than $H_w$, for example, being the same as $H_{wzone2}$.

The third zone (3c) has then an average wrinkle density $D_{wzone3}$ that is more than the average wrinkle density of the first zone $D_{wzone1}$; it may have an average wrinkle density $D_{wzone3}$ of about the same as the average wrinkle density of the elastic laminate portion (10) $D_w$ as a whole, but typically the third zone (3c) has an average wrinkle density that is more than said average $D_w$, and, for example, the same as (or more than) the average wrinkle density of the second zone $D_{wzone2}$.

The wrinkle densities and wrinkle heights can be determined by the Primos method described below.

Visualization of a transverse edge, i.e., a boundary, of a zone may also be done by use of the Primos method, as known in the art, and described below, by visualizing the line where either:

the height of the wrinkles on one side, (along 2 cm length), is smaller than the height of the wrinkles on the other side of said line, (along 2 cm length), or the line where on one side no wrinkles are present and on the other side wrinkles of a certain height are present (each along 2 cm length); or the density of the wrinkles on one side (along 2 cm length) is less than the density of the wrinkles on the other side of said line (along 2 cm length), or the line where on one side no wrinkles are present and on the other side wrinkles are presenting a certain density (each along 2 cm length).

The topsheet (20) comprises in one embodiment herein at least two elastic laminate portions (10), to form typically a pair of opposing, at least partially parallel, elastic laminate portions, (elasticated areas), such as described in copending application EP-A-1201212, and shown in FIGS. 1 to 5.

The elastic laminate portion (10) may extend from the longitudinal side edges of the opening(s) towards or completely to the front and back transverse edge of the topsheet. Thus, the elastic laminate portions (10) may be longer than the opening. The elastic laminate portions (10) may be positioned over the full length of the topsheet (20), or at least the part of the topsheet (20) which in use is intended to receive body exudates, typically the topsheet (20) minus the parts thereof which form (part of) the waist bands.

The elastic laminate portion (10) may be shaped such that it has a centre portion that is substantially parallel to the centre portion of the opposing elastic laminate portion (10).

Each of the two centre portions has a length, which may be 30% to 70% of the total length L1 of a corresponding elastic laminate portion (10) and/or 40% to 80% of the maximum length of the opening; hereby the total length of the elastic laminate portion (10) may be 70% to 90%, or from 80% to 90% or 85% of maximum length of the topsheet (20).

The front end portions of two opposing elastic laminate portions (10) may bend away from one another (in the plane of the topsheet (20)), so that the distance between the end edges of the opposing front end portions of two opposing elastic laminate portions (10) is larger that the distance between the centre portions of two opposing elastic laminate portions (10), and equally, the distance between the end edges of the opposing back end portions of two opposing elastic laminate portions (10) is larger that the distance between the centre portions of two elastic laminate portions (10).

The elastic laminate portion (10) is typically angled, as described herein, whereby it has a front and back angle with a longitudinal line through the centre straight part (or centre portion 0 of the elastic laminate portion (10) and parallel to the longitudinal axis of the topsheet (20), of between 10° and 40°, between 17° to 35°, or between 20° and 35°.

Figure 4:
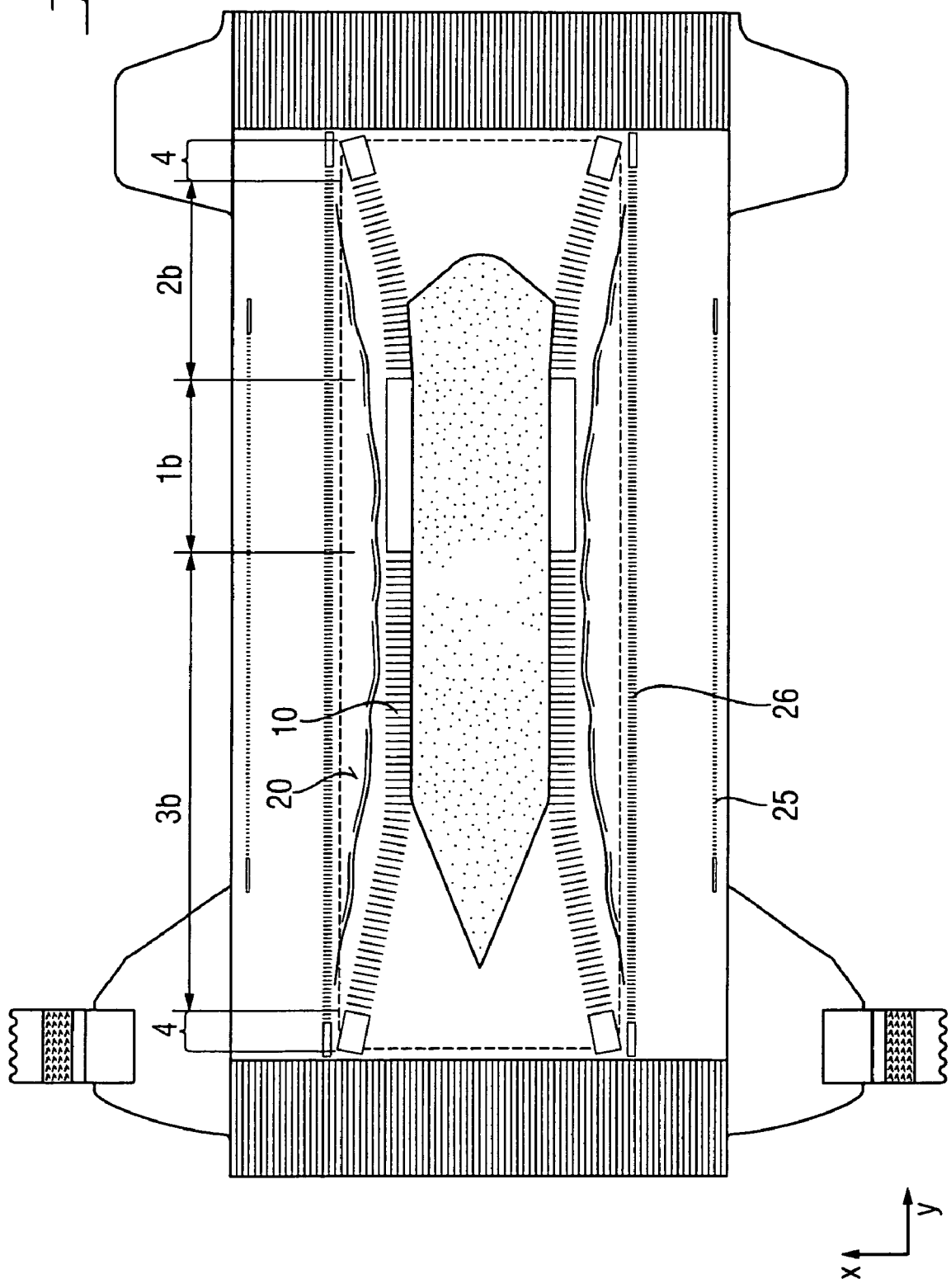
FIG. 4 shows a top-view of an alternative diaper, whereby the first zone (1b) is located slightly further towards the front waist region of the topsheet (20) and of the diaper, closer to where the genitals of a boy would be in use.

Such pair of opposing, angled elastic laminate portions (10) are herein referred to, as having an X-shape, and an X-shape is exemplified in FIGS. 3 and 4.

The topsheet (20) may comprise a pair of secondary elastics with optionally the requirements as set out herein above for the elastic laminate portions. These may be curved elastics with a radius R with a length of between 0.3 times the length of the topsheet (20) to 3.2 times the length of the topsheet (20).

The topsheet (20) may be any material compatible with the lamination to an elastic material (12). The topsheet (20) is, typically, not itself elastically stretchable in y-direction.

The topsheet (20) herein may even be relatively stiff material. In one embodiment, the topsheet (20) that is to form the elastic laminate portion (10) has a bending stiffness of at least 4 µNm, or even at least 8 µNm, or even at least 10 µNm or even at least 12 µNm. It may be a material with a relative high basis weight, namely at least of 10 gram per $m^2$ or even at least 15 gram per $m^2$, or even at least 20 gram per $m^2$ or even at least 25 gram per $m^2$. This may be determined by use of a KES-FB2 (pure bending) tester, available from Kato Tech Co Ltd, Japan, following the operating procedures of this equipment.

Suitable topsheets (20) for use with the present invention may comprise woven and non-woven materials of natural fibers (e.g., wood or cotton fibers) and/or synthetic fibers. The topsheet (20) may comprise thermoplastic polymer fibers, including, but not limited to: polyolefins, polyesters, polyurethanes, and polyamides.

The fibers may be spun bond, carded, wet-laid, melt blown, and/or hydro entangled, and/or otherwise processed as is known in the art. The topsheet (20) may comprise a nonwoven material that comprises at least meltblown fibers having a basis weight of at least 5 gram per $m^2$, or even at least 7 gram per $m^2$, or even at least 10 gram per $m^2$ or even 15 grams per $m^2$ (the maximum amount being limited by the basis weight of the topsheet (20) as a whole, as defined above).

The topsheet (20) may be air permeable. In certain executions herein, it may have high barrier properties.

The topsheet (20) may have micropores, that have a uniform pore size distribution with small micropores, i.e., the topsheet (20) has pores with a maximum pore size (bubble point diameter) of less than 100 µm, less than 75 µm, less than 50 µm and less than 25 µm. The pores may also have a mean pore size is less than 20 µm, less than 17 µm less than 13 µm or less than 10 µm.

It may be preferred that the topsheet (20) is a portion (10) of two or more sheets or webs. For example, the topsheet (20) may comprise at least two layers, one of which is a meltblown (M) layer and another is either a spunbond (S) or a carded (C) layer.

Examples of executions include SM SMS, SMMS, SSMS, SSMSS, SSMMS, CM or CMC non-wovens laminates. It may be preferred that one surface, web or layer of the topsheet (20) is treated with a surface energy reducing agent described herein.

The non-woven webs may be formed from polyethylene, polypropylene and/or polybutylene polymer fibers, or (a mixture of) fibers of a copolymers of polyethylene, polypropylene and/or polybutylene.

Materials used as topsheet (20) herein are, for example, a 34 gsm SMS polypropylene non-woven laminates, having a maximum pore size of 32 µm, an air permeability of 34 Darcy/mm, available from Pegas under the name Pegaphob 02 445 032; a 24 gsm SSMMS polypropylene non-woven laminates, having a maximum pore size of 57 µm, for example, available from Pegas under the name Pegaphob 02 445 024; a 34 gsm SSMMS polypropylene non-woven laminates, having a maximum pore size of 48 µm, for example, available from Pegas under the name Pegaphob 02 445 032; a 20 gsm web available from Sandler under the code VP21/00/75, having a maximum pore size of 22 µm; or a 20 gsm web available from Sandler under the code VP21/00/76, having a maximum pore size of 23 µm. Such materials may, for example, be treated with Dipolit, to reduce the surface energy of the materials.

It may also be preferred that the topsheet (20) comprises ingredients, which reduce friction between the wearer's skin and the topsheet (20), or in particular between the skin and the elastic laminate portion (10). Hereto, the topsheet (20), e.g., the laminate portion (10) or topsheet (20), may, for example, comprise a lotion, a fine powder, such as talcum powder, or wax.

The topsheet (20), topsheet (20) or laminate portion (10) may be treated with an agent to reduce its surface energy. For example, useful agent include fluorocarbons as described in U.S. Pat. No. 5,876,753, issued to Timmons et al. on Mar. 2, 1999; U.S. Pat. No. 5,888,591 issued to Gleason et al. on Mar. 30, 1999; U.S. Pat. No. 6,045,877 issued to Gleason et al. on Apr. 4, 2000. Other agents include silicone. Useful methods for applying the agent to the material, without reducing the air permeability, can be found in U.S. Pat. No. 5,322,729 and PCT Publication WO 96/03501. By way of example and not limitation, agents suitable for use with the present invention include fluorocarbons, siloxanes, polysiloxanes, fluorinated monomers and fluorinated polymers, hexafluoroethylene, hexafluoropropylene and vinyl fluoride and vinylidene fluoride, fluoroacrylate and fluoromethacrylate. Particularly suitable agents may include poly (tetra) fluoroethylene, fluorinated ethylene-propylene copolymers and/or fluorinated ethylene-tetrafluoroethylene copolymers.

The topsheet (20) may be hydrophobic and/or urine-impermeable.

In another embodiment, an elastic laminate portion (10) is formed by attaching one or more strands of elastic material (12) to a topsheet material to form a band of elastic material; such a formed laminate portion (10) is considered a single laminate portion (10) since it operates in use as such, e.g., the elastic strands are attached to the topsheet (20) in the same manner (e.g., parallel) and so close together that in use a laminate portion (10) is obtained that acts as a unitary elastic portion (10). Typically, the average distance between the elastic bands or stands in a unitary elastic laminate portion (10) is 1-5 mm, or 1-3 mm.

The width of the elastic laminate portions (10) will vary, typically depending on the exact dimensions of the topsheet (20) and/or of the article.

For example, for size 4 diapers the elastic laminate portion (10) in a topsheet (20) herein may, in stretched state, have an average width of about 3 mm to 50 mm, 3 mm to 40 mm, 3 mm to 30 mm or even 5 mm to 20 mm.

Any suitable elastic material (12) may be used for the purposes of the present invention, examples of such materials include VFE-CD, available from Tredegar, and L-86, available from Fulflex (Limerick, Ireland), L-89, available from Fulflex.

The elastic materials (12) used herein typically have a thickness (e.g., gauge) of at least 20 microns, at least 40 microns, or even at least 60 microns, typically up to about 300 microns, or even up to 200 microns or even up to 150 microns. Suitable materials for use with the present invention may have a thickness of about 70 to 100 microns.

The inventors found that by introducing one or more zones (1, 2) of reduced maximum elongation, or no elongation at all, and having typically smaller wrinkles and/or wrinkle densities, reduced pressure marks are obtained. However, the overall elastic profile of the topsheet (20) with the elastic laminate portions (10) and of the article can be maintained. Thus, the topsheet (20) with the elastic laminate portion (10) and/or the laminate portion (10) herein is such it typically has the following elastic profile, despite the first zone (1) of reduced elongation; either:

a) 1.5 Lt by a first load force of less than 1.1N or even less than 0.6N, 3.0 Lt by a first load force of less than 2.1N or even 1.1N and 4.5 Lt by a first load force of less than 3.0N or even less than 1.5N and a second unload force at 4.5 Lt of more than 0.9N, a second unload force at 3.0 Lt of more than 0.5N and a second unload force at 1.5 Lt of more than 0.1N.

(Said elastic profile obtainable by the method set out in co-pending application EP1201212-A, whereby Lt is the contracted length of the component, herein referred to as $L_c$). or:

b) 0.25 $L_s$ by a first load force of less than 0.6 N, 0.55 $L_s$ by a first load force of less than 5N or even less than 3.5 N and 0.8 $L_s$ by a first load force of less than 10.0N or even less than 7.0N and a second unload force at 0.55 $L_s$ of more than 0.4N, and a second unload force at 0.80 $L_s$ of more than 1.4N, or even more than 2.0N.

(Said elastic profile obtainable by the method set out in co-pending application EP1201212-A, whereby $L_s$ is as specified herein.)

The topsheet (20) or elastic laminate portion (10) has a force profile such that it has a first load force at 200% elongation of 1.6 N or less, and a second unload force at 200% elongation of 0.5 N or more.

Process

The topsheet (20) or laminate portion (10) can be obtained by, for example, a process comprising the steps of:

a. obtaining a topsheet material that is such that it has its maximum length dimension;

b. obtaining an elastic material (12) and elongating at least one first part thereof, by an elongation of less than 0.3, or leaving at least said first part non-elongated, said part having an absolute contracted length $L_{czone1}$ (in y-direction) of at least 2 cm; and c. elongating at least a second part thereof such with an elongation of at least 0.7;

d. applying said first parts as obtained in step b. to the topsheet material to form a first zone (1), e. applying said second parts as obtained in step b. to the topsheet material to form a second zone (2), to thus obtain an elastic laminate portion (10) with at least said first zone (1) and said second zone (2) of different elongation.

Hereby, step d. may be applied prior to step c. Also, step d. and optionally step e. may be applied prior to step b.

This is further shown in FIGS. 9 to 12.

The elastic material (12) may be attached to the topsheet material by any known method, including adhesive or heat bonding. They may be attached such that no attachment portions (4) are obtained that do not have any wrinkles, or such that only small attachment portions (4) are obtained, having a length (in direction of length of the elastic laminate portion (10)) of less than 1 cm, or even less than 0.5 mm.

A suitable method of attaching elastic bands or strands to a topsheet material is described in co-pending European application 03022089.1, filed 1 Oct. 2003, because that may also reduce any pressure marks by the second and third or further zones with the higher elongation and elasticity.

Figure 14:
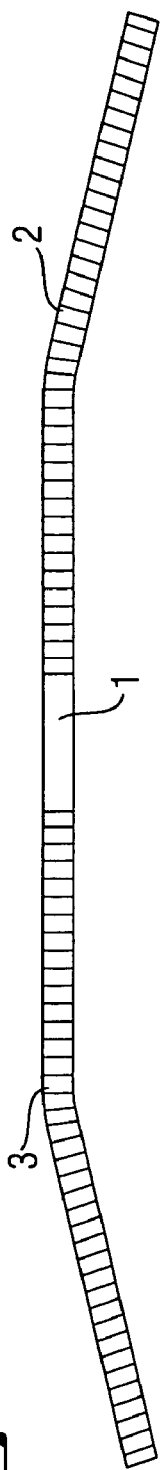
FIG. 14 shows this laminate portion of FIG. 13 at an average elongation of about 0.5.
Figure 16:
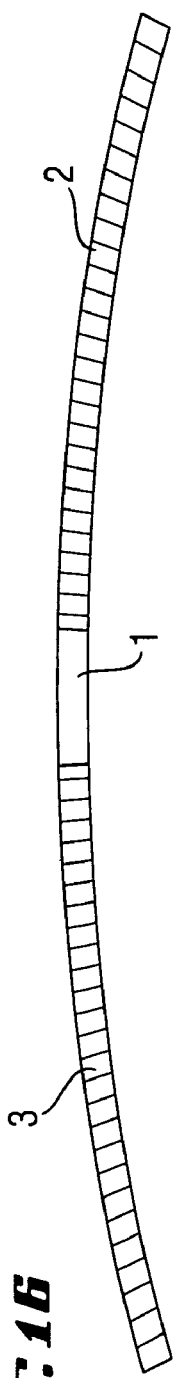
FIG. 16 shows this laminate portion of FIG. 15 at an average elongation of about 0.5.

Test Methods:

Method to Stretch to Its Fully Stretched Length (in Order to Define and Determine (the Position of the) Zones, $L_s$ and $L_{szonme1,2,...x}$, and Elongations) or to an Elongation of $\epsilon=0.5$:

For the calculations set out above, either the laminate portion (10) as a whole (when straight), a straight part thereof (when comprising straight angled parts, as in FIGS. 13 and 14), or sections (when curved, as in FIGS. 15 and 16) thereof—hereinafter referred to as sample—will be stretched by applying a force thereto. This is done as follows.

The topsheet (20) (comprising said "sample(s)") or if possible the elastic laminate portion(s) (10) thereof (comprising said "sample(s)") are obtained by removing this from the absorbent article such that the elongation potential, wrinkle height and wrinkle density are not changed.

It is left for 24 hours at 25° C. and 50% humidity, prior to the elongation/stretching step below, which is subsequently performed under the same conditions.

Measurement of lengths of sections/samples can be done with a micrometer screw.

(Each) sample to be tested is placed length-wise (in the direction of stretch) between two tweezers or, if the width of the sample is more than 1 cm, between two clamps of a width of 1 cm, one on each end, such that contact area of the tweezers/clamp and the sample is at the most 1 mm for clamps and 0.5 mm for tweezers in the direction of stretch (length). The exact distance between the start of one clamp or tweezers to the beginning of the other clamp or tweezers is measured. This is the contracted length of the sample, e.g., of the laminate portion, the straight part thereof or section thereof, i.e., 2 cm, as marked between the marker pen lines.

Then, the sample is stretched to its maximum elongation (e.g., when the supporting topsheet material (13) reaches its maximum length and the length of the sample and the distance between the clamps is measured, and the elongation $\epsilon$ is calculated.

For straight samples, the clamps or tweezers are moved in the y-direction of the length of the straight samples, such that the length direction is the direction of the elongation force.

For curved samples, the clamps are moved along the force line as determined above.

Elongation of $\epsilon=0.5$:

The densities and wrinkle heights are measured on an elastic laminate portion (10) when it has an "elongation $\epsilon$ of 0.5", which means herein the following.

If the elastic laminate portion (10) is straight, the topsheet (20) and/or laminate portion (10) as a whole is elongated or stretched to the length that it has an elongation $\epsilon=0.5$ (e.g., if $L_c$ is 20 cm, the laminate portion (10) is stretched to $L_s=30$ cm,). This laminate portion can then be tested in the method below.

If the elastic laminate portion (10) has straight parts that are connected by angles, as described above and shown in the FIGS. 1 to 5 and 13 and 14, each straight section is elongated by an elongation of 0.5, or if this is not possible (e.g., if one straight section coincides with a first zone (1) with hardly any or no elongation potential, as shown in FIGS. 5 and 8), to its maximum elongation (which should thus be less than 0.5). Then, this laminate portion can be tested in the method below.

If the elastic laminate portion (10) is curved, as described above and shown in FIGS. 15 and 16, each 2 cm section is elongated (by use of tweezers or clamps) to an elongation of 0.5, or if this is not possible, to its maximum elongation (which should be less than 0.5). Then, this laminate portion (10) can be tested in the method below.

In each case, the stretched elastic laminate portion (10) is fixed it this partially stretched position of $\epsilon=0.5$ by conventional means onto a testing surface (e.g., glue, pin) and then the tweezers used to stretch the elastic laminate portion are carefully removed, ensuring the position of the elastic laminate portion is not moved.

Defining the Zones of Different Wrinkle Height or Density; and Quantifying these Parameters The following described a method to visualize the boundaries of the zones (1, 2) herein, and/or a method to determine the wrinkle height and winkle density of the laminate portion (10) of the topsheet (20), sections and zones thereof.

Each sample with the elongation of 0.5 as defined and obtained by the method above, is examined by use of PRIMOS and its data acquisition software, following the manufacture's instructions manual, using a 13×18 mm lens.

The PRIMOS equipment and software will calculate the average wrinkle height and density of the sample, e.g., of the laminate as a whole or a section thereof, or part thereof. Then, the first and second zones can be identified, following the method outlined above for the elongation of the zones. The average wrinkle height and density of each section and identified zone (e.g., one or more sections) can be calculated.

If the elastic laminate portion (10) has an average width of more than 3 mm, then the measurement above is only done on the inner 70% of the width of the laminate portion, along its full length.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article, the disposable absorbent article comprising:
  a. a first waist region; a second waist region; and a pair of outermost longitudinal edges connecting the first waist region and the second waist region;
  b. a pair of elongate outer elastic portions respectively disposed inwardly of said outermost longitudinal edges in the x-direction;
  c. a topsheet including an opening therethrough, the opening having longitudinal edges; and
  d. an elastic laminate portion formed by elastic material attached to the topsheet, the elastic laminate portion being positioned along at least part of the longitudinal edges of the opening, the elastic laminate portion having an absolute contracted length $L_c$, a fully stretched absolute length $L_s$, and a maximum elongation $\epsilon$ of at least about 0.6, the elastic laminate portion including a first zone having a first zone absolute contracted length $L_{czone1}$, a first zone fully stretched length $L_{szone1}$ and a maximum first zone elongation $\epsilon_{zone1}$, and a second zone having a second zone absolute contracted length $L_{czone2}$, a second zone fully stretched length $L_{szone2}$, and a maximum second zone elongation $\epsilon_{zone2}$, wherein $\epsilon_{zone1}$ is less than or equal to about 50% of $\epsilon$, $\epsilon_{zone2}$ is greater than $\epsilon$, and $L_{czone1}$ and $L_{czone2}$ are each at least about 2 cm;
  wherein the topsheet and the elastic laminate portion are elastically stretchable in a first direction.

2. The absorbent article of claim 1, wherein the elastic laminate portion includes a third zone positioned such that the first zone is between the second zone and the third zone, the third zone having a maximum third zone elongation $\epsilon_{zone3}$ of more than $\epsilon$.

3. The absorbent article of claim 1, wherein the article has a crotch region and a y-direction, the first zone being positioned in the crotch region of the article or in the 40% or 30% of the article nearest either the first waist region or the second waist region in the y-direction.

4. The absorbent article of claim 1, further comprising a diaper or adult incontinence garment having a front transverse edge, a back transverse edge and a y-direction, the opening being an elongated slit and the topsheet including at least two elastic laminate portions wherein each of the elastic laminate portions extend along the y-directional edges of the opening towards or to the front transverse edge and/or back transverse edge in an X-shape.

5. The absorbent article of claim 1, wherein the topsheet is hydrophobic and includes a nonwoven laminate, the nonwoven laminate including one or more spunbond nonwoven layers and one or more meltblown nonwoven layers.

6. The absorbent article of claim 1, wherein the topsheet has a force profile such that it has a first load force at 200% elongation of 1.6 N or less, and a second unload force at 200% elongation of 0.5 N or more.

7. A disposable absorbent article, the disposable absorbent article comprising:
  a. a first waist region; a second waist region; and a pair of outermost longitudinal edges connecting the first waist region and the second waist region;
  b. a pair of elongate outer elastic portions respectively disposed inwardly of said outermost longitudinal edges in the x-direction;
  c. a topsheet including an opening therethrough, the opening having longitudinal edges; and
  d. an elastic laminate portion being formed by elastic material attached to the topsheet, the elastic laminate portion having a partially stretched state, the elastic laminate portion being positioned along at least part of the longitudinal edges of the opening, the elastic laminate portion having an absolute contracted length $L_c$, a fully stretched absolute length $L_s$, and a maximum elongation $\epsilon$ of at least about 0.6, the elastic laminate portion including a first zone having a first zone absolute contracted length $L_{czone1}$, a first zone fully stretched length $L_{szone1}$ and a maximum first zone elongation $\epsilon_{zone1}$, and a second zone having a second zone absolute contracted length $L_{czone2}$, a second zone fully stretched length $L_{szone2}$, and a maximum second zone elongation $\epsilon_{zone2}$, wherein $\epsilon_{zone1}$ is less than or equal to about 50% of $\epsilon$, the $\epsilon_{zone2}$ is greater than $\epsilon$, and $L_{czone1}$ and $L_{czone2}$ are each at least about 2 cm;
  wherein the topsheet and the elastic laminate portion are elastically stretchable in a first direction;
  wherein the elastic laminate portion, when in the partially stretched state such that $\epsilon$ is equal to about 0.5, has wrinkles with an average wrinkle height $H_w$, the first zone having no wrinkles or wrinkles with a first zone average wrinkle height $H_{wzone1}$, wherein $H_{wzone1}$ is less than about 50% of $H_w$; and wherein the elastic laminate portion, when in the partially stretched state such that $\epsilon$ is equal to about 0.5, has a wrinkle density $D_w$ and a first zone wrinkle density $D_{wzone1}$, wherein $D_{wzone1}$ is zero or less than about 50% of $D_w$.

* * * * *